(12) United States Patent
Chayen et al.

(10) Patent No.: US 6,369,107 B1
(45) Date of Patent: *Apr. 9, 2002

(54) COMBINED USE OF DICLOFENAC AND TRIBENOSIDE TO TREAT OSTEOARTHRITIS

(75) Inventors: Joseph Chayen, Surrey; Lucille Bitensky, deceased, late of Surrey; by Martin Roy Kagan, executor, Teddington, all of (GB)

(73) Assignee: KS Biomedix Ltd., Surrey (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/484,011

(22) Filed: Jan. 18, 2000

Related U.S. Application Data

(63) Continuation of application No. 08/849,513, filed as application No. PCT/GB95/02955 on Dec. 18, 1995, now Pat. No. 6,034,122.

(30) Foreign Application Priority Data

Dec. 16, 1994 (GB) ............................................. 9425487

(51) Int. Cl.⁷ ......................... A61K 31/20; A61K 31/34; A61K 31/70
(52) U.S. Cl. ......................... 514/561; 514/473; 514/27
(58) Field of Search ................................... 514/27, 561

(56) References Cited

U.S. PATENT DOCUMENTS 4,464,376 A    8/1984   Sunshine et al.
6,034,122 A *  3/2000   Chayen et al. .............. 514/473

FOREIGN PATENT DOCUMENTS

DE    36 14 278    10/1986
EP    0 433 817    6/1991

OTHER PUBLICATIONS

D.A. Kalbhen, "Arthrosis: medication and cartilagenous degeneration," Le Concours Medical, vol. 108, No. 38, pp. 3273–3277, 1986.
Daniel Burkhardt et al., "Laboratory Evaluation of Antiarthritic Drugs as Potential Chondroprotective Agents," Seminars in Arthritis and Rheumatism, col. 17. No. 2, supp. 1, pp. 3–34, Nov. 1987.
M.G. Chamber et al., "Chondrocytic monomine oxidase activity in the development of natural murine osteoarthritis," Int. J. Exp. Path., 73, 115–123, 1992.
J. Chayen et al., "Modulation of Murine Osteoarthritis," Cel Biochemistry and Function, vol. 14, pp. 57–61, 1996.
CA:98949; Kalbhen et al. (1983).

* cited by examiner

Primary Examiner—Frederick Krass
Assistant Examiner—Donna Jagoe
(74) Attorney, Agent, or Firm—Oliff & Berridge, PLC

(57) ABSTRACT

Effective synergistic amounts of (i) a compound that acts on the chondrocytes such as a fenamic acid derivative and (ii) a compound that reduces the water content of the chondrocyte matrix such as one based on a sugar nucleus with bulky substituents, as a combined preparation, are useful for simultaneous, separate or sequential use in the treatment of osteoarthritis.

19 Claims, No Drawings

COMBINED USE OF DICLOFENAC AND TRIBENOSIDE TO TREAT OSTEOARTHRITIS

This is a Continuation of application Ser. No. 08/849,513 filed Jan. 5, 1998, now U.S. Pat. No. 6,034,122 which in turn is a PCT-U.S. National Stage application of international application no. PCT/GB95/02955 filed Dec. 18, 1995. The entire disclosure of the prior applications is hereby incorporated by reference herein in its entirety.

FIELD OF THE INVENTION

This invention relates to compositions for use in the treatment of osteoarthritis (OA).

BACKGROUND OF THE INVENTION

Many drugs are known for the treatment of osteoarthritis, but in general their effectiveness is low, especially if side-effects are to be avoided. A known drug of this type is diclofenac sodium.

In normal articular cartilage (human as well as murine), monoamine oxidase in chondrocytes can be found located precisely in mitochondria. During the development of the natural disease in mice, these granules become larger and apparently burst, the monoamine oxidase (MAO) activity becomes distributed through the cytoplasm of the chondrocytes and even into the surrounding matrix. This was described by Chambers et al, Int. J. Exp. Path. 73:115–123 (1992), who related the MAO activity in the medial as against that in the (normal) lateral cartilage in untreated mice and in those treated with diclofenac.

The presumption from these findings was as follows: when circulating pharmacologically-active amines, such as adrenalin, enter normal chondrocytes they are detoxified by the MAO inside the mitochondria. Such detoxification requires both the close association of the MAO with the coenzyme FAD (flavine adenine dinucleotide) and the close presence of a peroxidase to remove the $H_2O_2$ generated by the MAO activity. When the MAO occurs in the matrix of the cartilage, it is unlikely to be functional, because (i) it may have been disrupted from its coenzyme (FAD), and (ii) if it were to be operative, it would be generating $H_2O_2$ which would be damaging to the matrix.

When diclofenac sodium was given to mice, there was a marked improvement in the localisation of the MAO in the potentially osteoarthritic cartilage. There was no sign of activity in the general cytoplasm or in the matrix.

It was suggested that the diclofenac molecule might become split to yield monoamines which would be a weak substrate for the relevant enzyme, and act as competitive inhibitors of the MAO activity. However, diclofenac sodium did not stop the development of OA in these mice.

Diclofenac sodium is related to fenamic acid. Derivatives of fenamic acid have been used as anti-inflammatory agents, particularly influencing the cyclooxygenase and/or 5-lipoxygenase systems; see U.S. Pat. No. 5,114,958.

SUMMARY OF THE INVENTION

The present invention is based on the postulate that two influences are involved in the development of OA: a cellular and an extracellular factor. The first is improved by, for example, diclofenac sodium or another compound having the same effect; the second, namely oedema of the matrix, is improved by, for example, tribenoside or another compound having the same effect. Whether or not the postulate is correct, it has been found experimentally that administration of diclofenac resulted in at least 9/10 mice having severe OA, but that a combination of the two drugs has resulted in 7/9 mice having no sign of OA.

A composition according to the present invention comprises compounds that respectively act on the chondrocytes and that reduce the water content of the chondrocyte matrix. These compounds can be given simultaneously or sequentially, for the prevention or treatment of OA.

DESCRIPTION OF THE INVENTION

The two active components used in this invention may be formulated as a mixture or independently, in kit form, for simultaneous, separate or sequential administration to a subject. Each compound may be formulated together with a suitable pharmaceutically-acceptable solid, semi-solid or liquid excipient, for oral, parenteral or topical administration. Depending on the desired route of administration, any of a variety of carriers may be used. Examples of such materials are known to those skilled in the art, and include powders such as talc, and aqueous carriers. The composition may be formulated, again in known manner, e.g. as a tablet, solution, suspension, ampoule, capsule or other unit dose. For example, 25, 50 and 75 mg tables of diclofenac sodium are already available.

An amount of each active component is given, that is effective for the desired treatment. Each compound may be given in an amount of 1 to 2000 mg/day, but this is merely a guide, and in any given case the amount will be chosen, if appropriate by the attending physician, having regard to factors such as the age, health and weight of the patient, and the severity of the complaint under treatment. In general, suitable dosages of the active components can simply be determined.

Compositions of this invention are suitable for use in the treatment of osteoarthritis in humans and in animals, e.g. domesticated and farm animals such as dogs, cats and horses.

Although the invention will be specifically described with relation to the use of diclofenac, other suitable materials include the series of fenamic acid derivatives since all have the relevant nitrogen atom between two benzene rings. Oxicams come into this category, as does piroxicam. Basically any compound which has the general formula $R_1$—NH—$R_2$ would be a candidate, depending on its toxicity and on how readily $R_1$ or $R_2$ could be removed in the body to yield a pseudo-substrate for monoamine oxidase ("pseudo-substrate" is one which can bind to the enzyme but which can be only slowly oxidised by it, or not oxidised at all). Basically this concept applies to any molecule which either alone or with minimal breakage of the molecule, could yield an aromatic amine which might be a weak substrate for monoamine oxidase.

Similarly, biologues of tribenoside (glyvenol) may be used, e.g. compounds similarly based on a sugar nucleus, with bulky substituents.

The extra-cellular factor was studied by quantitative interference microscopy, as described by Ross, "Phase Contrast and Interference Microscopy for Cell Biologists" Arnold: London, p.36 (1967). This form of microscopy allows the investigator to measure the dry mass, per unit area (Cs), in selected regions of a section or of a cell. This measurement then allows the assessment of water content (Cw):

$$Cw = 100 - 0.75\ Cs$$

Such quantitative microscopic interferometric measurements showed that the concentration of dry mass in the affected, medial cartilage of these mice was markedly less than that of the unaffected lateral cartilage (Chambers et al, 1992). The water content of the latter was very similar to that found in both medial and lateral tibial cartilages of CBA mice which were not prone to osteoarthritis.

Feeding STR/ORT mice with diclofenac sodium has no effect on the dry mass per unit area (and therefore, on the water content). On the one hand, however, feeding such mice with tribenoside markedly increased the content of dry mass of the medial cartilage, making the dry mass/unit area even of the medial cartilage virtually equivalent to that of the lateral cartilage of these mice, or to the cartilages of CBA mice (Table 1). On the other hand, such feeding did not improve the localisation of MAO activity. Mice were then fed with diclofenac sodium and tribenoside: both the water content and the MAO activity in the medial cartilage of such mice were "normal"; i.e. equivalent to the activities in the lateral cartilage. The consequences of this treatment, in three separate experiments, were that whereas 9/10 of the STR/ORT mice of this colony, and of this age, had damaged cartilage, only 2/7 that had been treated in this way showed any sign of damage. Results are shown in Table 1, i.e. the dry mass per µm in the matrix of cartilages of the tibial plateau of STR/ORT mice after various treatments. Three mice were treated with diclofenac (Df) alone, four with tribenoside (Tb) alone, and four with both (Df+Tb).

TABLE 1

| Treatment | Mass pg/unit area in the | |
| --- | --- | --- |
| | medial cartilage | lateral cartilage |
| 4 CBA mice | 2.8–2.97 | 2.8–2.97 |
| Vehicle | 0.41 | — |
| Df | 0.51 | — |
| Df | 0.50 | — |
| Df | 0.52 | 2.73 |
| Df + Tb | 2.71 | 3.18, 3.05* |
| Df + Tb | 2.10 | 2.93 |
| Df + Tb | 2.52 | 2.93 |
| Df + Tb | 3.14 | — |
| Tb | 2.54, 2.76, 2.58, 2.77* | — |
| Tb | 2.29 | 2.84 |
| Tb | 2.44 | — |
| Tb | 3.14 | — |

*duplicate sections
—covered by meniscus or no lateral in the section

What is claimed is:

1. A composition comprising effective synergistic amounts of (i) a compound that is a fenamic acid derivative and (ii) a compound that is tribenoside, as a combined preparation, for simultaneous, separate or sequential use in the treatment of osteoarthritis.

2. A composition comprising a mixture of compounds (i) and (ii) as defined in claim 1, and a physiologically-acceptable carrier, for therapeutic use.

3. A composition according to claim 1, wherein compound (i) is diclofenac sodium.

4. A composition according to claim 1, wherein compound (ii) is tribenoside.

5. A method for the treatment of osteoarthritis in a subject, which comprises administering to said subject effective synergistic amounts of a composition comprising (i) a compound that is a fenamic acid derivative and (ii) a compound that is tribenoside.

6. A method according to claim 5, wherein compound (i) is diclofenac sodium.

7. A method according to claim 5, wherein compound (ii) is tribenoside.

8. A composition according to claim 1, wherein compound (i) is an oxicam.

9. A composition according to claim 1, wherein compound (i) is an piroxicam.

10. A composition according to claim 1, wherein compound (i) is a compound of the formula $R_1$—NH—$R_2$, wherein the $R_1$ and $R_2$ groups can be removed in vivo to form a pseudo-substrate for monoamine oxidase.

11. A method according to claim 5, wherein compound (i) is an oxicam.

12. A method according to claim 5, wherein compound (i) is an piroxicam.

13. A method according to claim 5, wherein compound (i) is a compound of the formula $R_1$—NH—$R_2$, wherein the $R_1$ and $R_2$ groups can be removed in vivo to form a pseudo-substrate for monoamine oxidase.

14. A composition comprising effective synergistic amounts of (i) a compound that acts on chondrocytes and is a fenamic acid derivative and (ii) a compound that reduces water content of a chondrocyte matrix and is tribenoside, as a combined preparation, for simultaneous, separate or sequential use in the treatment of osteoarthritis.

15. A composition according to claim 14, wherein compound (i) is an oxicam.

16. A composition according to claim 14, wherein compound (i) is an piroxicam.

17. A composition according to claim 14, wherein compound (i) is a compound of the formula $R_1$—NH—$R_2$, wherein the $R_1$ and $R_2$ groups can be removed in vivo to form a pseudo-substrate for monoamine oxidase.

18. A composition comprising effective synergistic amounts of (i) a compound that is a fenamic acid derivative and (ii) a compound that is tribenoside.

19. A method for the treatment of a subject, which comprises administering to said subject effective synergistic amounts of a composition comprising (i) a compound that is a fenamic acid derivative and (ii) a compound that is tribenoside.

* * * * *